US006847842B1

(12) United States Patent
Rodenhiser et al.

(10) Patent No.: US 6,847,842 B1
(45) Date of Patent: Jan. 25, 2005

(54) METHOD AND APPARATUS FOR REDUCING EARLY RECURRENCE OF ATRIAL FIBRILLATION WITH DEFIBRILLATION SHOCK THERAPY

(75) Inventors: Kristen Rodenhiser, Redmond, WA (US); Mark Schwartz, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/570,645

(22) Filed: May 15, 2000

(51) Int. Cl.$^7$ ............................................. A61N 1/08
(52) U.S. Cl. ............................................................ 607/5
(58) Field of Search ................................ 600/515, 516, 600/518, 519, 521; 607/2, 4, 5, 7, 9, 11, 14, 15, 17, 25, 27

(56) References Cited

U.S. PATENT DOCUMENTS

| | | | |
|---|---|---|---|
| 3,937,226 A | 2/1976 | Funke | 128/419 D |
| 4,202,340 A | 5/1980 | Langer et al. | 128/419 |
| RE30,387 E | 8/1980 | Denniston, III et al. | 128/419 |
| 4,378,020 A | 3/1983 | Nappholz et al. | 128/419 PG |
| 4,407,288 A | 10/1983 | Langer et al. | 128/419 PG |
| 4,488,561 A | 12/1984 | Doring | 128/786 |
| 4,523,593 A | 6/1985 | Rueter | 128/419 PG |
| 4,548,203 A | 10/1985 | Tacker, Jr. et al. | 128/419 |
| 4,554,922 A | 11/1985 | Prystowsky et al. | 128/419 |
| 4,559,946 A | 12/1985 | Mower | 128/419 D |
| 4,595,009 A | 6/1986 | Leinders | 128/419 |
| 4,637,397 A | 1/1987 | Jones et al. | 128/419 D |
| 4,641,656 A | 2/1987 | Smits | 128/419 D |
| 4,662,382 A | 5/1987 | Sluetz et al. | 128/785 |
| 4,665,919 A | 5/1987 | Mensink et al. | 128/419 PG |
| 4,693,253 A | 9/1987 | Adams | 128/419 D |
| 4,708,145 A | 11/1987 | Tacker, Jr. et al. | 128/419 D |
| 4,763,646 A | 8/1988 | Lekholm | 128/419 PG |
| 4,774,952 A | 10/1988 | Smits | 128/419 D |
| 4,775,950 A | 10/1988 | Terada et al. | 364/578 |
| 4,787,389 A | 11/1988 | Tarjan | 128/419 PG |
| 4,788,980 A | 12/1988 | Mann et al. | 128/419 PG |
| 4,800,883 A | 1/1989 | Winstrom | 128/419 D |
| 4,819,643 A | 4/1989 | Menken | 128/419 P |
| 4,821,723 A | 4/1989 | Baker, Jr. et al. | 128/419 D |
| 4,821,724 A | 4/1989 | Whigham et al. | 128/419 |
| 4,827,932 A | 5/1989 | Ideker et al. | 128/419 D |
| 4,834,100 A | 5/1989 | Charms | 128/419 D |
| 4,880,004 A | 11/1989 | Baker, Jr. et al. | 128/419 PG |
| 4,903,700 A | 2/1990 | Whigham et al. | 128/419 |
| 4,940,054 A | 7/1990 | Grevis et al. | 128/419 PG |
| 4,944,300 A | 7/1990 | Saksena | 128/419 D |

(List continued on next page.)

FOREIGN PATENT DOCUMENTS

| | | | | |
|---|---|---|---|---|
| EP | 0347708 | 12/1989 | | A61B/5/02 |
| EP | 0436517 | 7/1991 | | |
| EP | 0467652 | 1/1992 | | A61N/1/368 |

(List continued on next page.)

OTHER PUBLICATIONS

*Metrix Model 3020 Implantable Atrial Defibrillator*, Physician's Manual, InControl. Inc., Redmond, WA,(1998),pp. 4–24–4–27.

(List continued on next page.)

Primary Examiner—Jeffrey R. Jastrzab
Assistant Examiner—Frances P. Oropeza
(74) Attorney, Agent, or Firm—Schwegman, Lundberg, Woessner & Kluth, P.A.

(57) ABSTRACT

An apparatus and method for delivering electrical shock therapy in order to treat atrial tachyarrhythmias such as fibrillation in which atrial defibrillation pulses are delivered within a maximum pre-shock R—R synchronization interval. The method has been found to reduce the incidence of early recurrence of atrial fibrillation (ERAF).

12 Claims, 2 Drawing Sheets

U.S. PATENT DOCUMENTS

| | | | |
|---|---|---|---|
| 4,949,719 A | 8/1990 | Pless et al. | 128/419 |
| 4,951,667 A | 8/1990 | Markowitz et al. | 128/419 PG |
| 4,967,747 A | 11/1990 | Carroll et al. | 128/419 |
| 4,972,835 A | 11/1990 | Carroll et al. | 128/419 |
| 4,984,572 A | 1/1991 | Cohen | 128/419 D |
| 4,996,984 A | 3/1991 | Sweeney | 128/419 D |
| 5,007,422 A | 4/1991 | Pless et al. | 28/419 PG |
| 5,018,523 A | 5/1991 | Bach, Jr. et al. | 128/419 |
| 5,042,480 A | 8/1991 | Hedin et al. | 128/419 |
| 5,048,521 A | 9/1991 | Pless et al. | 128/419 PG |
| 5,077,667 A | 12/1991 | Brown et al. | 364/413.05 |
| 5,085,213 A | 2/1992 | Cohen | 128/419 D |
| 5,103,819 A | 4/1992 | Baker et al. | 128/419 |
| 5,111,811 A | 5/1992 | Smits | 128/419 D |
| 5,111,812 A | 5/1992 | Swanson et al. | 128/419 D |
| 5,117,824 A | 6/1992 | Keimel et al. | 128/419 D |
| 5,154,485 A | 10/1992 | Fleishman | 297/445 |
| 5,161,527 A | 11/1992 | Nappholz et al. | 128/419 PG |
| 5,161,528 A | 11/1992 | Sweeney | 128/419 D |
| 5,163,428 A | 11/1992 | Pless | 128/419 D |
| 5,165,403 A | 11/1992 | Mehra | 128/419 D |
| 5,178,140 A | 1/1993 | Ibrahim | 128/419 D |
| 5,179,945 A | 1/1993 | Van Hofwegen et al. | 128/419 |
| 5,188,105 A | 2/1993 | Keimel | 128/419 |
| 5,193,535 A | 3/1993 | Bardy et al. | 128/419 D |
| 5,193,536 A | 3/1993 | Mehra | 128/419 D |
| 5,205,283 A | 4/1993 | Olson | 128/419 PG |
| 5,207,219 A * | 5/1993 | Adams et al. | 128/419 |
| 5,265,600 A | 11/1993 | Adams et al. | 607/4 |
| 5,269,300 A | 12/1993 | Kelly et al. | 607/4 |
| 5,275,621 A | 1/1994 | Mehra | 607/5 |
| 5,277,231 A | 1/1994 | Dostalek | 140/106 |
| 5,282,836 A | 2/1994 | Kreyenhagen et al. | 607/4 |
| 5,282,838 A | 2/1994 | Hauser et al. | 607/9 |
| 5,285,780 A | 2/1994 | Tsuji et al. | 607/13 |
| 5,314,448 A | 5/1994 | Kroll et al. | 607/5 |
| 5,330,508 A | 7/1994 | Gunderson | 607/14 |
| 5,332,400 A * | 7/1994 | Alferness | 607/5 |
| 5,339,820 A | 8/1994 | Henry et al. | 128/696 |
| 5,346,506 A | 9/1994 | Mower et al. | 607/7 |
| 5,350,401 A | 9/1994 | Levine | 607/4 |
| 5,354,316 A | 10/1994 | Keimel | 607/15 |
| 5,366,485 A | 11/1994 | Kroll et al. | 607/5 |
| 5,370,124 A | 12/1994 | Dissing et al. | 128/696 |
| 5,370,667 A | 12/1994 | Alt | 607/19 |
| 5,374,282 A | 12/1994 | Nichols et al. | 607/18 |
| 5,376,103 A | 12/1994 | Anderson et al. | 607/5 |
| 5,383,907 A | 1/1995 | Kroll | 607/5 |
| 5,395,373 A | 3/1995 | Ayers | 607/8 |
| 5,396,902 A | 3/1995 | Brennen et al. | 128/772 |
| 5,403,355 A | 4/1995 | Alt | 607/9 |
| 5,403,356 A | 4/1995 | Hill et al. | 607/14 |
| 5,411,524 A * | 5/1995 | Rahul | 607/4 |
| 5,431,682 A | 7/1995 | Hedberg | 607/5 |
| 5,431,685 A | 7/1995 | Alt | 607/6 |
| 5,439,006 A | 8/1995 | Brennen et al. | 128/772 |
| 5,439,483 A | 8/1995 | Duong-Van | 607/5 |
| 5,441,518 A | 8/1995 | Adams et al. | 607/5 |
| 5,441,521 A | 8/1995 | Hedberg | 607/6 |
| 5,456,706 A | 10/1995 | Pless et al. | 607/122 |
| 5,458,622 A | 10/1995 | Alt | 607/15 |
| 5,464,429 A | 11/1995 | Hedberg et al. | 607/4 |
| 5,466,245 A | 11/1995 | Spinelli et al. | 607/17 |
| 5,476,498 A | 12/1995 | Ayers | 607/122 |
| 5,476,499 A | 12/1995 | Hirschberg | 607/123 |
| 5,480,413 A | 1/1996 | Greenhut et al. | 604/14 |
| 5,486,198 A | 1/1996 | Ayers et al. | 607/5 |
| 5,489,293 A | 2/1996 | Pless et al. | 607/5 |
| 5,500,008 A | 3/1996 | Fain | 607/5 |
| 5,507,780 A | 4/1996 | Finch | 607/5 |
| 5,522,853 A | 6/1996 | Kroll | 607/5 |
| 5,545,182 A | 8/1996 | Stotts et al. | 607/5 |
| 5,545,204 A | 8/1996 | Cammilli et al. | 607/123 |
| 5,549,642 A | 8/1996 | Min et al. | 607/5 |
| 5,554,174 A | 9/1996 | Causey, III | 607/5 |
| 5,560,370 A | 10/1996 | Verrier et al. | 128/705 |
| 5,562,709 A | 10/1996 | White | 607/5 |
| 5,584,864 A | 12/1996 | White | 607/5 |
| 5,591,215 A | 1/1997 | Greenhut et al. | 607/14 |
| 5,609,613 A | 3/1997 | Woodson et al. | 607/19 |
| 5,609,621 A | 3/1997 | Bonner | 607/122 |
| 5,617,854 A | 4/1997 | Munsif | 128/642 |
| 5,620,468 A | 4/1997 | Mongeon et al. | 607/5 |
| 5,620,469 A | 4/1997 | Kroll | 607/7 |
| 5,626,136 A | 5/1997 | Webster, Jr. | 128/642 |
| 5,628,778 A | 5/1997 | Kruse et al. | 607/123 |
| 5,662,119 A | 9/1997 | Brennen et al. | 128/772 |
| 5,662,687 A | 9/1997 | Hedberg et al. | 607/5 |
| 5,674,250 A | 10/1997 | de Coriolis et al. | 607/7 |
| 5,683,431 A | 11/1997 | Wang | 607/28 |
| 5,683,445 A | 11/1997 | Swoyer | 607/125 |
| 5,690,686 A | 11/1997 | Min et al. | 607/5 |
| 5,699,014 A | 12/1997 | Haefner et al. | 330/253 |
| 5,709,215 A | 1/1998 | Perttu et al. | 128/708 |
| 5,713,924 A | 2/1998 | Min et al. | 607/4 |
| 5,759,202 A | 6/1998 | Schroeppel | 607/126 |
| 5,772,590 A | 6/1998 | Webster, Jr. | 600/374 |
| 5,772,693 A | 6/1998 | Brownlee | 607/123 |
| 5,776,164 A * | 7/1998 | Ripart | 607/5 |
| 5,778,881 A | 7/1998 | Sun et al. | 128/696 |
| 5,782,239 A | 7/1998 | Webster, Jr. | 128/642 |
| 5,782,887 A | 7/1998 | van Krieken et al. | 607/25 |
| 5,797,967 A | 8/1998 | KenKnight | 607/4 |
| 5,814,081 A | 9/1998 | Ayers et al. | 607/5 |
| 5,824,031 A | 10/1998 | Cookston et al. | 607/122 |
| 5,840,079 A | 11/1998 | Warman et al. | 607/4 |
| 5,843,153 A | 12/1998 | Johnston et al. | 607/122 |
| 5,849,032 A | 12/1998 | Van Venrooij | 607/123 |
| 5,853,426 A | 12/1998 | Shieh | 607/5 |
| 5,865,838 A | 2/1999 | Obel et al. | 607/5 |
| 5,868,680 A | 2/1999 | Steiner et al. | 600/518 |
| 5,873,842 A | 2/1999 | Brennen et al. | 600/585 |
| 5,893,882 A | 4/1999 | Peterson et al. | 607/14 |
| 5,902,331 A | 5/1999 | Bonner et al. | 607/122 |
| 5,922,014 A | 7/1999 | Warman et al. | 607/123 |
| 5,925,073 A | 7/1999 | Chastain et al. | 607/122 |
| 5,951,471 A | 9/1999 | de la Rama et al. | 600/381 |
| 5,955,218 A | 9/1999 | Crespi et al. | 429/219 |
| 5,964,795 A | 10/1999 | McVenes et al. | 607/122 |
| 5,968,079 A | 10/1999 | Warman et al. | 607/5 |
| 5,987,354 A | 11/1999 | Cooper et al. | 607/5 |
| 5,991,657 A | 11/1999 | Kim | 607/5 |
| 5,999,850 A | 12/1999 | Dawson et al. | 607/4 |
| 5,999,854 A | 12/1999 | Deno et al. | 607/18 |
| 5,999,858 A | 12/1999 | Sommer et al. | 607/122 |
| 6,006,122 A | 12/1999 | Smits | 600/373 |
| 6,006,137 A | 12/1999 | Williams | 607/119 |
| 6,021,354 A | 2/2000 | Warman et al. | 607/123 |
| 6,047,210 A * | 4/2000 | Kim et al. | 607/4 |
| 6,055,457 A | 4/2000 | Bonner | 607/126 |
| 6,067,471 A | 5/2000 | Warren | 607/5 |
| 6,070,104 A | 5/2000 | Hine et al. | 607/123 |
| 6,076,014 A | 6/2000 | Alt | 607/4 |
| 6,081,745 A | 6/2000 | Mehra | 607/4 |
| 6,081,746 A | 6/2000 | Pendekanti et al. | 607/5 |
| RE36,765 E | 7/2000 | Mehra | 607/4 |
| 6,085,116 A | 7/2000 | Pendekanti et al. | 607/5 |
| 6,085,119 A | 7/2000 | Scheiner et al. | 607/122 |
| 6,091,988 A | 7/2000 | Warman et al. | 607/5 |
| 6,115,628 A | 9/2000 | Stadler et al. | 600/517 |
| 6,115,630 A | 9/2000 | Stadler et al. | 600/521 |

| | | |
|---|---|---|
| 6,161,037 A | 12/2000 | Cohen .................... 600/513 |
| 6,246,906 B1 | 6/2001 | Hsu et al. ................. 607/4 |
| 6,249,699 B1 | 6/2001 | Kim ....................... 607/4 |
| 6,256,534 B1 | 7/2001 | Dahl ...................... 607/5 |
| 6,272,380 B1 | 8/2001 | Warman et al. ............ 607/5 |
| 6,275,734 B1 | 8/2001 | McClure et al. ........... 607/27 |
| 6,280,391 B1 | 8/2001 | Olson et al. .............. 600/509 |
| 6,430,438 B1 | 8/2002 | Chen et al. ............... 607/5 |
| 6,430,449 B1 | 8/2002 | Hsu et al. ................. 607/126 |
| 6,459,932 B1 | 10/2002 | Mehra ..................... 607/5 |
| 6,526,317 B2 | 2/2003 | Hsu et al. ................. 607/4 |
| 6,556,862 B2 | 4/2003 | Hsu et al. ................. 607/4 |
| 6,584,350 B2 | 6/2003 | Kim et al. ................. 607/5 |
| 6,587,720 B2 | 7/2003 | Hsu et al. ................. 607/4 |
| 6,721,596 B1 | 4/2004 | Girouard et al. ........... 607/4 |
| 2003/0004551 A1 | 1/2003 | Chen ...................... 607/14 |
| 2003/0199928 A1 | 10/2003 | Hsu et al. ................. 607/5 |
| 2004/0015192 A1 | 1/2004 | Kim et al. |

FOREIGN PATENT DOCUMENTS

| | | | |
|---|---|---|---|
| EP | 0522693 | 1/1993 | ........... A61N/1/39 |
| EP | 0550343 | 7/1993 | ........... A61N/1/38 |
| EP | 0550344 | 7/1993 | ........... A61N/1/39 |
| EP | 0588125 | 9/1993 | ........... A61N/1/39 |
| EP | 0588124 | 3/1994 | ........... A61N/1/39 |
| EP | 0594269 | 4/1994 | |
| EP | 0606688 | 7/1994 | |
| EP | 0770412 | 5/1997 | |
| EP | 0813886 | 12/1997 | ........... A61N/1/05 |
| FR | 2528708 | 12/1983 | |
| WO | WO-93/02746 | 2/1993 | .......... A61N/1/368 |
| WO | WO-93/20888 | 10/1993 | .......... A61N/1/365 |
| WO | WO-95/28987 | 11/1995 | ........... A61N/1/39 |
| WO | WO-95/28988 | 11/1995 | ........... A61N/1/39 |
| WO | WO-WO97/01373 | 1/1997 | |
| WO | WO-97/01373 | 1/1997 | |
| WO | WO-98/48891 | 11/1998 | .......... A61N/1/362 |

OTHER PUBLICATIONS

"Blanking Circuit Diagram Illustrating a Circuit in the PRXII Defibrillator", Cardiac Pacemakers, Inc., Reqt, Hybrid, Analog 530370 Rev 02,p. 32.

"Blanking Circuit Diagram Illustrating a Circuit in the VIGOR Pacemaker", Sold by Cardiac Pacemakers Inc.,.

Allessie, M , et al., "Regional Control of Atrial Fibrillation by Rapid Pacing in Conscious Dogs", Circulation, 84 (4), (Oct. 1991),pp. 1689–1697.

Ayers, Gregory M., et al., "Ventricular Proarrhythmic Effects of Ventricular Cycle Length and Shock Strength in a Sheep Model of Transvenous Atrial Defibrillation", Circulation, 89 (1), (Jan. 1994),413–422.

Circulation, 85 (5), (May 1992),pp. 1865–1878.

Frazier, D.W., et al., "Stimulus–Induced Critical Point— Mechanism for Electrical Initiation of Reentry in Normal Canine Myocardium", Journal of Clinical Investigation, 83, (Mar. 1989),pp. 1039–1052.

Greenhut, S. , et al., "Effectiveness of a Ventricular Rate Stabilization Algorithm During Atrial Fibrillation in Dogs", Pace Abstract, Abstract No. 60,(1996), 1 p.

Hayes, D L., et al., "Pacemaker Timing Cycles", In: Cardiac Pacing, Edited by Kenneth A. Ellenbogen, M.D., published by Blackwell Science,(1992),263–308.

Hsia, Peng W., et al., "Absolute Depolarization Vector Characteristics Associated with Successful Defibrillation: Evidence of a Vulnerable Period During Ventricular Fibrillation", Circulation, 82 (4), Supplement III, Abstracts, Abstract No. 2933,(Oct. 1990),p. III–738.

Hsia, Peng W., et al., "Genesis of Slgmoidal Dose–Response Curve During Defibrillation by Random Shock: A Theoretical Model Based on Experimental Evidence for a Vulnerable Window During Ventricular Fibrillation", Pace, 13, NASPE Young Investigator Awardee–1990,(Oct. 1990),pp. 1326–1342.

Hsia, Peng W., et al., "Improved Nonthoracotmy Defibrillation Based on Ventricular Fibrillation Waveform Characteristics", PACE, 18—NASPE Abstracts, Abstract No. 29,(Apr. 1995),p. 803.

Jones, Douglas L., et al., "Ventricular Fibrillation: The Importance of Being Coarse?", Journal of Electrocardiology, 17 (4), (1984),pp. 393–399.

Kenknight, B H., et al., "Regional Capture of Fibrillating Ventricular Myocardium", Circulation Research, 77 (4), (Oct. 1995),pp. 849–855.

Kuelz, Kathy W., et al., "Integration of Absolute Ventricular Fibrillation Voltage Correlates with Successful Defibrillation", IEEE Transactions on Biomedical Engineering, 41 (8), (Aug. 1994), pp. 782–791.

Mower, Morton M., et al., "Synchronization of Low–Energy Pulses to Rapid Deflection Signals as a Possible Mechanism of Subthreshold Ventricular Defibrillation", Abstracts of the 55th Scientific Sessions, Abstract No. 298,(1982),p. II–75.

Singer, Igor, et al., "The Automatic Implantable Cardioverter Defibrillator: T Wave Sensing in the Newest Generation", PACE, 11, Part I, (Nov. 1988),pp. 1584–1591.

Tang, A S., et al., "Three–Dimensional Potential Gradient Fields Generated by Intracardiac Catheter and Cutaneous Patch Electrodes", Circulation, 85 (5), (May 1992),pp. 1857–1864.

Thakor, N. V., et al., "Optimal QRS Detector", Medical & Biological Engineering & Computing, 21, (May 1983),pp. 343–350.

Wharton, J M., et al., Cardiac Potential and Potential Gradient Fields Generated by Single, Combined, and Sequential Shocks During Ventricular.

Defibrillation, Circulation, 85 (4), (Apr. 1992),pp. 1510–1523.

Wittkampf, F.H.M., et al., "Rate Stabilization by Right Ventricular Pacing in Patients with Atrial Fibrillation", Pace, vol. 9, Part II, (Nov.–Dec. 1986), 1147–1153.

* cited by examiner

METHOD AND APPARATUS FOR REDUCING EARLY RECURRENCE OF ATRIAL FIBRILLATION WITH DEFIBRILLATION SHOCK THERAPY

FIELD OF THE INVENTION

This invention pertains to methods for treating atrial tachyarrhythmias. In particular, the invention relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and also incorporate cardiac pacing functionality.

The most dangerous tachyarrythmias are ventricular tachycardia and ventricular fibrillation, and ICDs have most commonly been applied in the treatment of those conditions. ICDs are also capable, however, of detecting atrial fibrillation and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat AF offer a number of advantages to certain patients, including convenience and greater efficacy.

An ICD terminates atrial fibrillation by delivering a shock pulse to electrodes disposed in or near the atria. The resulting depolarization also spreads to the ventricles, however, and there is a risk that such an atrial shock pulse can actually induce ventricular fibrillation, a condition much worse than atrial fibrillation. This risk can be reduced by delaying the delivery of an atrial shock pulse until the intrinsic ventricular rhythm is below a specified maximum rate and then delivering the shock synchronously with a sensed ventricular depolarization.

Another problem associated with defibrillation shock therapy is early recurrence of atrial fibrillation or ERAF. ERAF is defined as the recurrence of atrial fibrillation within a few minutes after successful cardioversion with atrial shock therapy. Certain patients are more prone than others to experience ERAF, and these patients may experience difficulty with repeated atrial defibrillation therapy. Reducing the incidence of ERAF would improve the efficacy of atrial defibrillation and expand the population of patients for whom an ICD is an acceptable therapy option. It is this problem with which the present invention is primarily concerned.

SUMMARY OF THE INVENTION

The present invention is a method and apparatus for delivering atrial defibrillation therapy in which an atrial shock pulse is delivered within a specified maximum time interval after a preceding sensed ventricular depolarization or ventricular pace (R wave). In one embodiment, an R—R interval, defined as the time elapsed between a previous R wave and a present R wave, is measured after each sensed R wave. The atrial defibrillation shock pulse is then delivered synchronously with an R wave that occurs within a specified time window with respect to the previous R wave as defined by specified minimum and maximum R—R interval values. In another embodiment, an atrial shock pulse is delivered at a specified time after the previous R wave unless inhibited by an intrinsic ventricular depolarization occurring before the specified time. The atrial defibrillation shock can also be delivered in synchrony with a ventricular pace delivered at a specified time after the previous R wave unless inhibited by an R wave occurring before that time.

In one embodiment, an R—R interval, defined as the time elapsed between a previous R wave and a present R wave, is measured after each sensed R wave. The atrial defibrillation shock pulse is then delivered synchronously with an R wave that occurs within a specified time window with respect to the previous R wave as defined by specified minimum and maximum R—R interval values. In another embodiment, an atrial shock pulse delivered at a specified time after the previous R wave unless inhibited by an intrinsic ventricular depolarization occurring before the specified time. The atrial defibrillation shock can also be delivered in synchrony with a ventricular pace delivered at a specified time after the previous R wave unless inhibited by an R wave occurring before that time.

DETAILED DESCRIPTION OF THE INVENTION

The present invention is a method and apparatus for delivering atrial defibrillation shock therapy. As used herein, atrial defibrillation shock therapy should be taken to mean shock therapy for treating any atrial tachyarrhythmia, such as atrial flutter, as well as atrial fibrillation.

In order to avoid the possible induction of ventricular fibrillation, atrial defibrillation shocks are usually delivered synchronously with a sensed R wave and after a minimum pre-shock R—R interval. (The R—R interval is the time between the immediately preceding R wave and the presently sensed R wave, and an R wave may be regarded as either a spontaneously occurring depolarization or a ventricular pace.) This is done because the ventricle is especially vulnerable to induction of fibrillation by a depolarizing shock delivered at a time too near the end of the preceding ventricular contraction (i.e., close to the T wave on an EKG). Delivering the shock synchronously with a sensed R wave thus moves the shock away from the vulnerable period, but at a very rapid ventricular rhythm, the ventricular beats may be so close together that even synchronously delivered shocks may induce ventricular fibrillation. To prevent this, shocking can be delayed until the ventricular rhythm is slow enough to safely deliver the defibrillation pulse as determined by measuring the R—R interval. That is, a minimum limit value for the R—R interval is specified, and shocking is inhibited if the sensed R wave occurs after a shorter interval. Recent clinical data has shown, however, that the incidence of early recurrence of atrial fibrillation (ERAF) after atrial defibrillation is positively correlated with the length of the pre-shock R—R interval.

Figure 1A:
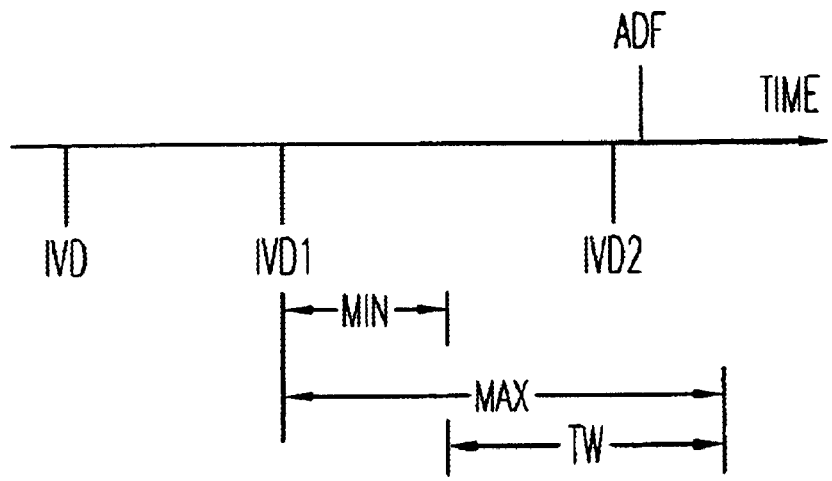
FIGS. 1A and 1B are timing diagrams illustrating embodiments of the invention.

In accordance with the present invention, atrial defibrillation shocks are delivered within a specified maximum time interval after a preceding sensed ventricular depolarization or ventricular pace (R wave). In one embodiment, the atrial defibrillation shock is delivered in synchrony with a sensed R wave. An R—R interval, defined as the time elapsed between a previous R wave and a present R wave, is measured after each sensed R wave. In contradistinction to previous methods, however, a shockable R—R interval is specified with both minimum and maximum limit values. The atrial defibrillation shock pulse is thus delivered synchronously with an R wave that occurs within a time window with respect to the previous R wave as defined by specified minimum and maximum R—R interval values. FIG. 1A is a diagram showing a sequence of intrinsic ventricular depolarizations IVD occurring during an episode of atrial defibrillation. After the depolarization labeled IVD1, a time window TW as defined by a minimum R—R interval MIN and a maximum R—R interval MAX is shown. This time window is considered a shockable R—R interval, and exemplary minimum and maximum limit values are 500 and 800 milliseconds, respectively. Thus, an atrial defibrillation shock ADF can be delivered in synchrony with an R wave IVD2 occurring within the shockable interval and with a reduced risk of causing either ventricular fibrillation or ERAF.

Figure 1B:
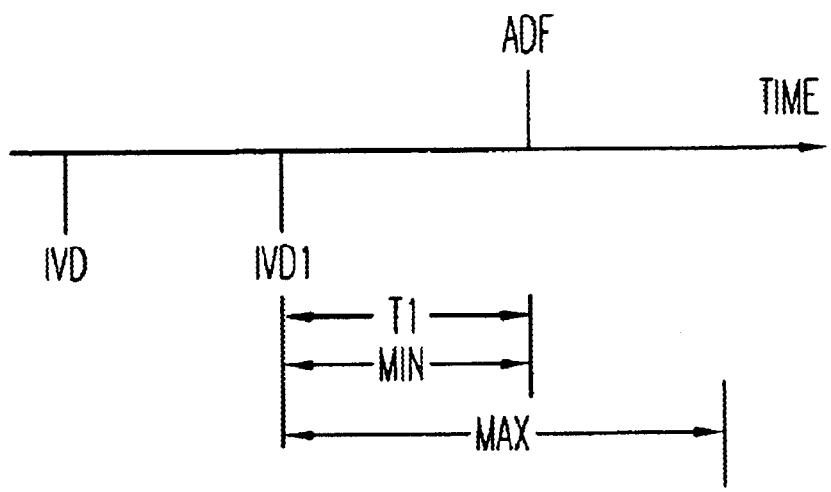

In another embodiment, an atrial shock pulse is delivered at a specified time after the previous R wave unless inhibited by an intrinsic ventricular depolarization occurring before the specified time. FIG. 1B shows another exemplary sequence of intrinsic ventricular depolarizations IVD occurring during an episode of atrial defibrillation. After the depolarization labeled IVD1, a specified time T1 is defined in which an atrial defibrillation shock ADF is to be delivered. The time T1 would preferably fall somewhere within the shockable R—R interval as defined above even though the atrial shock is not delivered in synchrony with an R wave. Delivering the atrial shock pulse at the time T1 thus reduces the risk of ERAF as in the first embodiment. Induction of ventricular fibrillation is prevented by both specifying the time T1 to be above a minimum value considered safe to shock and inhibiting the atrial shock if an intrinsic R wave occurs prior to the time T1. The atrial defibrillation shock can also be delivered in synchrony with a ventricular pace delivered at the specified time T1 after the previous R wave unless inhibited by an R wave occurring before that time.

Figure 2:
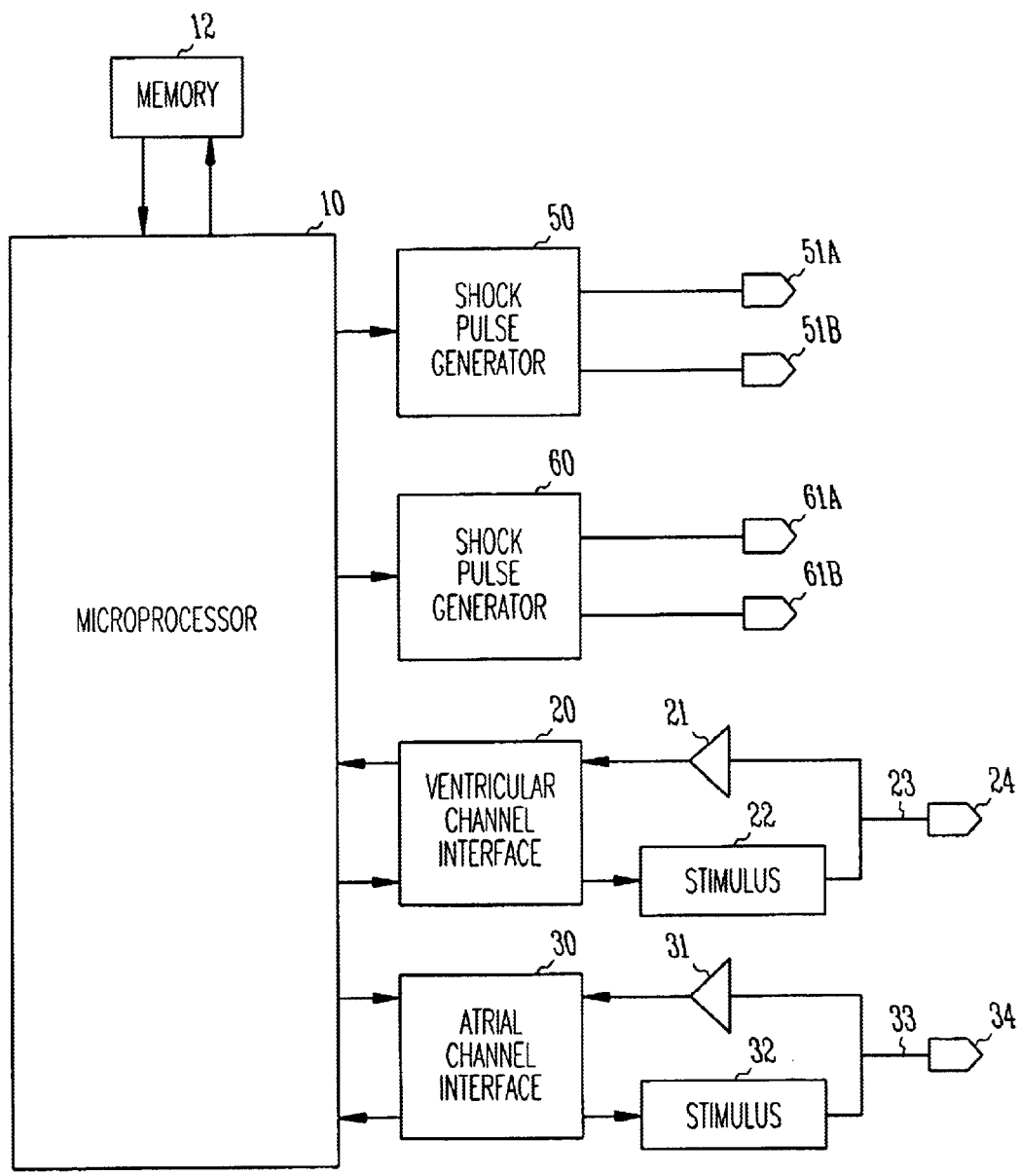
FIG. 2 is a system diagram of an implantable defibrillator.

FIG. 2 is a system diagram of a microprocessor-based implantable cardioverter/defibrillator device for treating atrial tachyarrthmias that also incorporates a pacemaker functionality. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used to control pacing and for measuring heart rate in order to detect tachyarrythmias such as fibrillation. The ICD detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. The defibrillation leads have along their length electrically conductive coils that act as electrodes for defibrillation stimuli. A similar shock pulse generator 60 and shock electrodes 61a and 61b are provided to deliver ventricular fibrillation therapy in the event of an induced ventricular fibrillation from atrial shock pulses.

The device depicted in FIG. 2 can be configured to deliver atrial defibrillation therapy in accordance with the invention as described above by appropriate programming of the microprocessor. Thus, once an episode of atrial fibrillation is detected with the atrial sensing channel, the device prepares to deliver an atrial defibrillation shock. As described above, the ventricular rhythm can monitored by measuring the R—R interval associated with each sensed R wave. If a sensed R wave occurs at an R—R interval longer than a specified minimum limit value and shorter than a specified maximum limit value, the interval is considered shockable so that the sensed R wave is safe to shock on. An atrial defibrillation shock can then delivered immediately so as to be practically synchronous with the sensed R wave. Alternatively, the atrial shock pulse can be delivered at a specified time after the preceding sensed R wave, either synchronously with a ventricular pace or not, unless inhibited by a sensed intrinsic R wave occurring prior to the time specified for delivering the atrial shock.

In another embodiment of the invention, an atrial defibrillation shock pulse is preceded by ventricular pacing in order to decrease the intrinsic ventricular rhythm to a rate at which the atrial defibrillation shock pulse can be more safely delivered. After atrial fibrillation is detected, a sequence of one or more ventricular pacing pulses is delivered at a rate intended to be above the intrinsic ventricular rate. After the last pacing pulse in the sequence is delivered, a compensatory pause is produced before the next intrinsic ventricular beat. The atrial defibrillation shock pulse can then be delivered synchronously with that beat if the sensed R wave occurs within the shockable R—R interval as defined by specified minimum and maximum limit value. In the embodiment where the atrial defibrillation pulse is to be delivered at a specified time after the preceding R wave, either with or without an accompanying ventricular pace, the compensatory pause also delays the next R wave so that inhibition of the atrial shock is less likely to occur.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for delivering atrial defibrillation therapy, comprising:

detecting an episode of atrial fibrillation;

sensing ventricular depolarizations (R waves);

delivering a first ventricular pacing pulse after a sensed R wave; and delivering an atrial defibrillation shock without an accompanying second ventricular pacing pulse at a specified time after the first ventricular pacing pulse but inhibiting the atrial defibrillation shock if a second R wave subsequent to the first ventricular pacing pulse occurs before the specified time.

2. The method of claim 1 wherein the specified time for delivering the atrial defibrillation shock is less than 800 milliseconds.

3. The method of claim 1 wherein the specified time for delivering the atrial defibrillation shock is greater than 500 milliseconds and less than 800 milliseconds.

4. The method of claim 1 wherein the first ventricular pacing pulse is preceded by one or more additional ventricular pacing pulses delivered after the sensed R wave at a rate greater than the measured intrinsic rate.

5. The method of claim 1 wherein the specified time for delivering the atrial defibrillation shock is less than 800 milliseconds.

6. The method of claim 5 wherein the specified time for delivering the atrial defibrillation shock is greater than 500 milliseconds and less than 800 milliseconds.

7. The method of claim 1 wherein the first ventricular pacing pulse is delivered after the sensed R wave at a rate above an intrinsic ventricular rate.

8. An apparatus for delivering atrial defibrillation therapy to an atrium, comprising:

sensing channels for sensing atrial and ventricular depolarizations (R waves);

a ventricular pacing channel for delivering ventricular pacing pulses;

an atrial defibrillation pulse generator and electrodes disposed in proximity to the atrium; and a controller for detecting atrial fibrillation and for controlling delivery of atrial defibrillation shocks and ventricular pacing pulses, wherein, upon detection of atrial fibrillation, the controller is configured to:

deliver a first ventricular pacing pulse after a sensed R wave; and deliver an atrial defibrillation shock without an accompanying second ventricular pacing pulse at a specified time after the first ventricular pacing pulse but inhibit the atrial defibrillation shock if an R wave subsequent to the first ventricular pacing pulse occurs before the specified time.

9. The apparatus of claim 8 wherein the specified time for delivering the atrial defibrillation shock is less than 800 milliseconds.

10. The apparatus of claim 8 wherein the specified time for delivering the atrial defibrillation shock is greater than 500 milliseconds and less than 800 milliseconds.

11. The apparatus of claim 8 wherein the controller is configured to deliver the first ventricular pacing pulse preceded by one or more additional ventricular pacing pulses delivered after the sensed R wave at a rate greater than the measured intrinsic rate.

12. The apparatus of claim 8 wherein the first ventricular pacing pulse is delivered after the sensed R wave at a rate above an intrinsic ventricular rate.

* * * * *

UNITED STATES PATENT AND TRADEMARK OFFICE
CERTIFICATE OF CORRECTION

PATENT NO.    : 6,847,842 B1
DATED         : January 25, 2005
INVENTOR(S)   : Rodenhiser et al.

It is certified that error appears in the above-identified patent and that said Letters Patent is hereby corrected as shown below:

Title page,
Item [56], References Cited, OTHER PUBLICATIONS, "Metrix Model 3020..." reference, delete "InControl." and insert -- InControl, --, therefor.

Column 2,
Line 43, after "pulse" insert -- is --.

Signed and Sealed this

First Day of November, 2005

JON W. DUDAS
*Director of the United States Patent and Trademark Office*